United States Patent [19]

Irgum et al.

[11] Patent Number: 4,666,856
[45] Date of Patent: May 19, 1987

[54] SO$_2$ DETERMINATION BY ADSORPTION USING ION EXCHANGE RESIN WITH PH BUFFERED CAPACITY

[76] Inventors: Knut Irgum, 9A, Kvartsvägen, S-902 42 Umeå; Mats J. Lindgren, 1, Häradshövdingegatan, S-902 45 Umeå, both of Sweden

[21] Appl. No.: 630,685

[22] Filed: Jul. 13, 1984

[30] Foreign Application Priority Data

Jul. 14, 1983 [SE] Sweden ............................ 8303981

[51] Int. Cl.$^4$ ............................................ G01N 30/96
[52] U.S. Cl. ................................. 436/122; 436/167; 436/178; 422/88; 502/402; 521/28
[58] Field of Search .......................... 422/59, 88, 91; 436/122, 168, 178, 167; 423/244 R; 502/402; 521/26, 28

[56] References Cited

U.S. PATENT DOCUMENTS

| | | |
|---|---|---|
| 3,558,279 | 1/1971 | McRae et al. |
| 3,951,859 | 4/1976 | Inaba et al. ........................ 502/402 |
| 3,960,762 | 6/1976 | Kroebel et al. ..................... 502/402 |
| 3,996,162 | 12/1976 | McCall ............................... 436/178 |
| 4,003,848 | 1/1977 | Cotter et al. ....................... 502/402 |
| 4,043,952 | 8/1977 | Ganslaw et al. .................... 502/402 |
| 4,081,403 | 3/1978 | Takegami et al. .................. 502/402 |
| 4,131,544 | 12/1978 | Elahi .................................. 436/178 |
| 4,272,486 | 6/1981 | Harman, III ......................... 422/91 |
| 4,340,483 | 7/1982 | Lukás et al. ........................ 502/402 |
| 4,481,297 | 11/1984 | Zucal et al. ........................ 436/167 |

FOREIGN PATENT DOCUMENTS 2446918  4/1975  Fed. Rep. of Germany .

OTHER PUBLICATIONS

"Apparatus for Determining Trace Sulfur Dioxide in Gas Mixtures", Hitachi, Ltd., Jpn. Kokai Tokkyo Koho JP, 79—Inorganic Anal. Chem., vol. 9, 1972, p. 785.

Primary Examiner—David L. Lacey
Attorney, Agent, or Firm—Cushman, Darby & Cushman

[57] ABSTRACT

A method of measuring a content of a compound such as gaseous sulfur dioxide in air comprising adsorbing the compound on a solid adsorbent, including a carrier consisting of a solid buffer of a partially regenerated ion exchanger.

In addition the solid adsorbent may comprise a stabilizer which is either a stabilizer for the compound intended to be adsorbed on the adsorbent or a stabilizer for a reaction product thereof formed in the adsorption.

17 Claims, 8 Drawing Figures

▲ = DESORBED DIRECTLY AND STORED IN A REFRIGERATOR;

■ = STORED ON THE TUBE IN A REFRIGERATOR;

◆ = STORED ON THE TUBE AT 20°C UNDER FLUORESCENT LIGHT.

SO₂ DETERMINATION BY ADSORPTION USING ION EXCHANGE RESIN WITH PH BUFFERED CAPACITY

This invention relates to a method of measuring a content of a compound in air and to a solid adsorbent for carrying out this measurement when the compound consists of sulfur dioxide. The invention also relates to the use of a partially regenerated ion exchanger as buffer in solid adsorbents.

The invention can be utilized for measuring contents of any compounds in air, preferably compounds in a gaseous state, but is especially well suited for measurement of sulfur dioxide in air, which measurement is fraught with considerable difficultie not always appearing when other materials are measured.

Consequently the invention is described in the following with reference to measurement of the content of sulfur dioxide in air.

Due to its high reactivity and tendency of being oxidized by oxygen in air, sulfur dioxide will be one of the more difficult compounds to sample in occupational hygienic measurements. Due to its irritating effect on the respiratory organs it will also be a great problem in industries where the gas is used or formed in the processes. The paper industry and the roasting industry are examples of such industries.

The sampling strategies may vary at sampling in connection with occupational hygiene. One can measure, on one hand, the long-time average values in premises, and, on the other hand, perform measurement with equipment carried by a person, which measurement has become of more and more current interest in recent years. Often the worker is exposed to the substance in a special working moment. Consequently one wants to know how great the exposure will be when this moment is carried out. Then there are small calibrated pumps capable of sampling air of a constant flow from the respiratory zone and fixing the compound of interest by means of a suitable material.

Such a fixation can be carried out by means of two different types of methods, viz. wet-chemical methods and using a solid adsorbent, respectively.

In wet-chemical methods gas scrubber flasks containing various absorption solutions are used, which flasks may be of a more or less sophisticated construction. However, the wet-chemical sampling has many disadvantages. It is especially awkward that the worker's freedom of movement is reduced if he carries the sampling equipment because the measurement must be carried out in such a way that the solution in the flask is not drawn into the pump, destroying both this and the sampling results. Moreover, the compounds used are often so toxic that spillage on one's skin may have serious consequences. Furthermore, there is an essential objection to wet-chemical sampling, i.e. it includes handling of the sample in the factory environment when the solution is to be transferred to and from the gas scrubber flask. This involves a considerable contamination risk and results in uncertainty in the analysis results.

The other type of methods, viz. sampling by using solid adsorbents, mostly means a modification of previously known wet-chemical methods so that they can be carried out on a suitable inert carrier. This is enclosed in a small tubular ampoule which is broken immediately prior to sampling. A suitable volume of air is drawn through the tube which has been placed in the respiratory zone in case it is carried by a person. After sampling, the tube is sealed again by means of small plastic sleeves and is sent to a laboratory for analysis. An advantage of this method is that all risk of spillage has been eliminated and that the contamination risk has been minimized. The method is well suited for measurement of low reactive and stable compounds but not for measurement of instable compounds, e.g. sulfur dioxide, as such compounds must be stabilized to prevent losses, e.g. by oxidation.

As pointed out above measurement of sulfur dioxide involves special problems. However, some methods for measurement of sulfur dioxide either based on wet-chemical technology or on the use of a solid adsorbent are described in literature.

I. Wet-chemical methods.

The classical West-Gaeke method (Philip W. West and G. C. Gaeke, "Fixation of Sulfur Dioxide as Disulfitomercurate (II) and Subsequent Colorimetric Estimation" Anal. Chem., 28 (1956) 1816–19.) for sampling and stabilization of sulfur dioxide is based on the formation of a complex with tetrachloromercurate (II) ions. In this case the absorption solution consists of 0.1-M HgCl₂ and 0.2-M NaCl. Sulfur dioxide in the sample will react according to the following reactions.

$$SO_2(g) + H_2O \rightleftharpoons 2H^+ + SO_3^{2-} \tag{1}$$

$$SO_3^{2-} + HgCl_4^{2-} \rightleftharpoons Hg(SO_3)Cl_2^{2-} + 2Cl^- \tag{2}$$

The sulfitodichloromercurate (II)-complex formed is relatively stable against oxidation under the current conditions. Considering the toxicity of the mercury this absorption solution will be far from ideal in wet-chemical sampling since, as mentioned above, the risk of spillage is considerable. Nevertheless this method has been used as standard in several countries, e.g., Sweden.

Recently Dasgupta et al (Purnendu K. Dasgupta, Kymron DeCesare and James C. Ullrey, "Determination of Atmospheric Sulfur Dioxide without Tetrachloromercurate(II) and the Mechanism of the Schiff Reaction." Anal. Chem., 52 (1980) 1912–22.) has published a method that should become an alternative of the West-Gaeke-method. Instead of mercury solution a weak buffered formaldehyde solution is used, where stabilization of sulfur dioxide as hydroxymethyl sulfonate is obtained after hydrolysis of the gas.

$$SO_2(g) + H_2O \rightleftharpoons H^+ + HSO_3^- \tag{3}$$

$$HSO_3^- + HCHO \rightleftharpoons CH_2(OH)SO_3^- \tag{4}$$

The compound formed has better stability than the disulfitodichloromercurate(II) ion used as a stabilizer in the West-Gaeke-method. It is also of great importance that the toxicity of the absorption solution is considerably less than in the first-mentioned method. According to these methods the final determination is carried out by formation of a colored complex with pararosaniline and formaldehyde which in West and Gaeke's method is added at the analysis, after which the colored complex is determined photometrically at 580 nm.

Moreover, the wet-chemical sampling basic glycerol (S. Atkins, "Determinattion of Sulfur Dioxide in Precence of Sulfur Trioxide." Anal. Chem., 22 (1950) 947.) and triethanolamine (M. Tokuda, K. Hirai, S. Fukui and S. Kanna; Eisei Kagaku, 24 (1978) 213; Chem. Abstr., 91 (1979) 111741r.) have been shown to give a moderate stabilization and, finally, hydrogen peroxide (J. D. Mulik et al, "Ion chromatographic determination of atmospheric sulfur dioxide." In Eugene Sawicki, J. D. Mulik and E. Wittgenstein, Editors, "Ion Chromatographic Analysis of Environmental Pollutants." Ann Arbor Sci. Publ. Inc., Ann Arbor, Mich. ISBN 0-250-40211-4.) has also been used an absorption solution for oxidation of sulfur dioxide to sulfate which can be determined e.g. by means of ion chromatography. One disadvantage of the last-mentioned method is that the possibility of distinguishing between the oxidation states (IV) and (VI) for sulfur in the sample has been lost.

II. Use of solid adsorbents

Even if some methods in which solid adsorbents are used for sampling of sulfur dioxide in working environments are described in literature, these are not used in practice to any large extent. One of these methods is built on stabilization of the gas through adsorption on active carbon impregnated with glycerol and potassium hydroxide (David L. Smith, Walter S. Kim and Richard E. Kupel, "Determination of sulfur dioxide by adsorption on a solid sorbent followed by ion chromatography analysis." J. Am. Ind. Hyg. Assoc., 41 (1980), 485–88.), but the documentation of the stability of the sampled gas is deficient. Moreover, active carbon is probably not suitable as a carrier material when sampling sulfur dioxide, as the inhomogeneous surface most probably will catalyze the oxidation of S(IV) or give an irreversible absorption.

According to another method, triethanolamine is used as stabilizer on 13-Å molecular sieves (Dutt V. Vinjamoori and Chaur-Sun Ling, "Personal Monitoring Method for Nitrogen Dioxide and Sulfur Dioxide with Solid Sorbent Sampling and Ion Chromatographic Determination." Anal. Chem., 53 (1981) 1689–91.). One problem with the use of molecular sieves as carrier material, at least together with carbonyl compounds, is that these will give an irreversible adsorption or oxidation of the sulfur dioxide. The documentation of the storability is also imperfect for this method.

The use of molecular sieves without stabilizer has been further described (Marilyn S. Black, Richard P. Herbst and Dian R. Hitchcock, "Solid Adsorbent Preconcentration and Gas Chromatographic Analysis of Sulfur Gases." Anal. Chem., 50 (1978) 848–51.). However, there is every reason to be critical of the results therein achieved, as no information is given about air humidity when testing the tubes. Dry sulfur dioxide is not subject to the oxidizing effect of oxygen in air the same way as in solutions or humid gas. Moreover, a gas chromatograph is required in the final determination step in addition to special desorption equipment.

When measuring the content of a certain compound in air, especially sulfur dioxide, sampling of air is obviously associated with many problems, and none of the methods known so far is a quite satisfactory solution to these problems.

Consequently it is one object of this invention to provide a simple and convenient method of measuring the content of a compound, e.g. a gas, in air, which method does not have the drawbacks of previously known methods.

According to the invention this object is achieved in such a way that the compound, the content of which is to be measured, is adsorbed on a solid adsorbent comprising a carrier and optionally also a stabilizing agent for the compound or a reaction product thereof formed in the adsorption, which reaction product is to be adsorbed on the adsorbent, said carrier consisting of a solid buffer of a partially regenerated ion exchange material; and that the adsorbed amount of the compound or its reaction product is measured thereafter in a known manner.

Another object of the invention is to provide a solid adsorbent for measuring the content of sulfur dioxide in air, which adsorbent shows good storability and on which $SO_2$ adsorbed in the form of hydrogen sulfite can be stabilized for subsequent analysis of the adsorbed amount.

This object is achieved according to the invention by means of a solid adsorbent consisting of a carrier which consists of a partially regenerated weak ion exchange material and of a stabilizer for adsorbed hydrogen sulfite which consists of an aldehyde, especially glyoxal.

The aadsorbent used with the method of the invention comprises a carrier consisting of a solid buffer of a partially regenerated ion exchange material. The ion exchange material can consist of a weak or strong ion exchange material which, due to the partial regeneration, has been given a buffer effect to a suitable pH-value depending on the compound to be stabilized.

An essential advantage achieved according to the invention is that the ion exchange material can operate as an anion-free buffer having a capacity widely exceeding that which can be achieved by conventional buffer systems, which buffer does not give rise to any anions in the solution in the final determination step which might have a disturbing influence. If ion chromatography is used as final determination method the anions can overload the column or, when using pararosaniline as final determination method, interference difficult to control may arise during the determination of sulfur dioxide.

A suitable ion exchange material with a buffer effect is a weak cation exchange material having a pka-value of about 5, whose concentration of active groups is about 4M in the form of carboxylic acid groups and which is regenerated in such a way that 50% of its active groups are in $H^+$-form and 50% in $Na^+$-form.

Examples of the ion exchange material are Amberlite IRC-84 (weak cation exchanger of polyacrylic acid type), Amberlite IRA-93 (weak anion exchanger with tertiary amino groups on a matrix of styrene-divinylbenzene copolymer), Amberlite IRC-50 (weak cation exchanger on polymethacrylate basis and Amberlite IRA-68 (weak anion exchanger of cross-linked polyacrylic acid esterified with a tertiary aminoalcohol), which are all commercially available (Serva, Heidelberg; FRG).

When the invention is utilized for measurement of sulfur dioxide in air the solid adsorbent must also include a stabilizing agent for hydrogen sulfite formed in the absorption, as the first step in the adsorption process is hydrolysis of $SO_2$ (g) with water that must be present on the adsorbent.

$$SO_2(g) + H_2O(l) \rightarrow HSO_3^-(aq) + H^+$$

The hydrogen sulfite formed is very instable in an aqueous solution and must be rapidly stabilized in some way or other. According to the invention this is achieved in such a way that the solid adsorbent also includes an aldehyde, preferably glyoxal, which is present in aqueous solution in the form of glyoxal hydrate. The stabilization takes place according to the following reaction The addition compound formed is stable against air oxidation during the current periods of time between sampling and analysis if pH≦8. Stability maximum lies at pH 4–5.

Other useful aldehydes are formaldehyde, acetaldehyde and chloral.

However, glyoxal is a preferred aldehyde for several reasons. As it only consists of two aldehyde functions it is the most efficient aldehyde per weight unit that can be selected. It is miscible with water in all proportions and can be bought in an aqueous solution of 30% with enough high quality to be used without additional purification. In glyoxal the reactivity of the carbonyl group is comparablle with that of the carbonyl group of formaldehyde, i.e. among the most reactive ones, which is an advantage in this connection.

Moreover, glyoxal is not subject to autooxidation by oxygen in air the same way as e.g. formaldehyde. It has been proved that if glyoxal is oxidized by oxygen in air air oxygen glyoxalic acid is formed. The aldehyde function thereof is stable against further oxidation to oxalic acid due to oxygen in air. In other words, an aldehyde group is present which is protected against autooxidation. This is essential when it is desired to make an adsorption tube containing a solid adsorbent, as the adsorbent must be capable of being stored for a long period before sampling if it is to be used commercially. Glyoxal is present in aqueous solutions in the form of a water addition product (glyoxal hydrate) which has the effect that the water retaining ability of the adsorbent is further improved. Glyoxal has also a low vapor pressure and thus will not evaporate from the tube in sampling. During measurment of SO₂ a combination of aldehyde and carrier compound consisting of a coating of 50% of 2-M glyoxal in water on Amberlite IRC-84, which is half regenerated, has been found to be suitable. This solid adsorbent is preferably used as enclosed in an adsorption tube, e.g. of glass, the compound being secured in the tube by means of a plug of polytetraflouroethylene-wool.

The final determination step in the method of the invention, i.e. the determination of adsorbed amount of the compound whose content is to be measured, or of a reaction product formed in the adsorption, is carried out in a known manner. Any known analysis method can be used and a suitable method is chosen due to such factors as the adsorbed compound, desirable sensitivity, accuracy of measurement and reliability of the method, economy etc. Examples of useful analysis methods are spectrophotometry, liquid, gas and ion chromatography.

In the case of sulfur dioxide two methods can particularly be mentioned, viz. ion chromatography and the pararosaniline method. Prior to the determination of adsorbed amount a desorption step is preferably carried out in a known manner in order to release adsorbed product from the adsorbent.

BRIEF DESCRIPTION OF THE DRAWINGS

In the following, an embodiment of the invention is described more closely concerning measurement of SO₂ and with reference to the enclosed drawings, wherein.

1. Preparation of the adsorbent:

Amberlite IRC-84 (20–50 mesh) p.a. (Serva, Heidelberg) was washed in water, filtered twice through Millipore and was then equilibrated twice in succession with 5 volumes 1-M HCl. The ion exchanger material, which was now in H⁺-form, was washed twice more with water, after which 2 volumes of 1-M NaOH were added for each volume of sedimented, swollen ion exchange compound. Stirring was started immediately and the substitution of Na⁺ for H⁺ was allowed to go until the reaction was completed, which was controlled continuously through the pH-value, which then fell below 6. When the reaction was finished the compound was washed repeatedly with water deionized with Millipore equipment, was filtered through a Büchner funnel and dried at 105° C. to a constant weight.

A solution of 2-M glyoxal, f. synthesis (Merck-Schuchardt, München), in water was prepared without further purification of the aldehyde. For each gram of dry "ion exchange buffer" prepared according to the above 1 ml of this solution was added. The product was left to stand for 24 hours at room temperature in order to swell. 200 mg of the final compound were then packed in a glass tube, 4 mm internal diameter×50 mm, which had been provided with a polyurethane plug at one end. Finally a small wad of PTFE-wool was inserted and the tube was sealed with plastic caps of the same type as those used for sealing the tubes after sampling. On a commercial scale it is possible to seal the tubes hermetically by melting together the ends.

II. Generation of a test atmosphere of SO₂(g):

As a source of sulfur dioxide, permeation tubes of fluorinated ethylene polymer filled with SO₂(l) under pressure were used. The permeation tube was placed in a furnace in which the set temperature of 30° C. could be maintained within 0.05° C. When the temperature was kept at a constant, sulfur dioxide penetrated the walls of the tube at a constant velocity. The gas generated in such a way was diluted in a dynamical gas dilution system with suitable proportions of air which had been purified with molecular sieves and allowed to pass a bed of silica gel to remove sulfur dioxide. For preparation of mixtures of different relative humidity it was diluted with water saturated air of the same quality. Relative humidity was measured by means of an instrument built for the purpose (Knut Irgum: "Instrument for Relative Humidity Measurement." Anal. Chem. 55 (1983) 1186–87.).

To monitor the content of sulfur dioxide in the gas mixture prepared in this way a coulometric titrator and adsorption in a 50-mM glyoxal solution in a gas scrubber flask and a following determination according to the pararosaniline method as described below were used. The coulometric cell could be in the line for continuous measurement of sulfur dioxide and in this way it was easy to determine break-through volumes by measuring on the gas after it had passed the tube.

For the application of sulfur dioxide to the tubes pumps were used of a type which is frequently used with sampling equipment carried by a person. In all tests these pumped with a flow of 200 ml/min. The flows were calibrated each day with bubble meters. In the storage tests the tubes were stored in room temperature under the light of fluorescent tubes and in refrigerators at +4° C.

III. Experiments of determination of breakthrough volumes:

This is one of the most important tests which should be carried out on a solid adsorbent, as this volume restricts the air amount which can be sampled with the tubes. The breakthrough volume will therefore have a direct influence on the detection limit that can be reached by means of the method. As indicated above a coulometric cell was connected in the line after the adsorption tube during the application of $SO_2$, and in this way the $SO_2$-content in the gas that had passed the tube could be followed continuously. This enabled plotting of curves which show the adsorption of $SO_2$ as a function of the time and consequently sampled volume.

As water is included as an initial step in the stabilizing reaction and accordingly must be present on the tube, a breakthrough will be obtained when this has dried away from the tube. For this reason the relative air humidity will have a great importance for how great a volume can be sampled without breakthrough. In commercial use the tubes are prepared with a back-up section of the same amount downstream of the analytical section where it can be seen by means of an analysis thereof if a breakthrough has taken place.

Breakthrough tests were carried out at different air humidities and temperatures. The results of these experiments are given in FIGS. 2a-c. In these tests 200 mg adsorbent with a 2M glyoxal/dry carrier ratio 1:1 (v/w) and a test atmosphere of 5 mg $SO_2(g)/m^3$ were used.

Figure 2A:
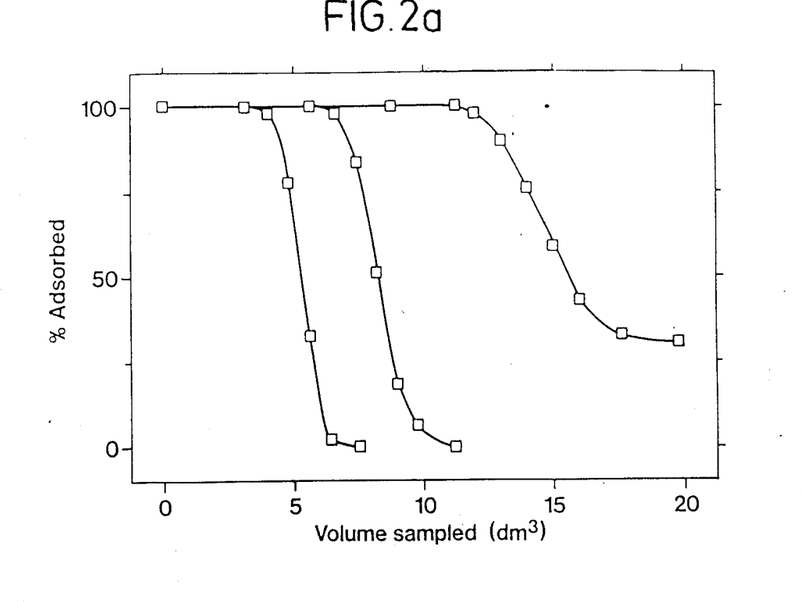
FIGS. 2a–c show breakthrough volumes at different temperatures and relative humidities of the test atmosphere.
Figure 2B:
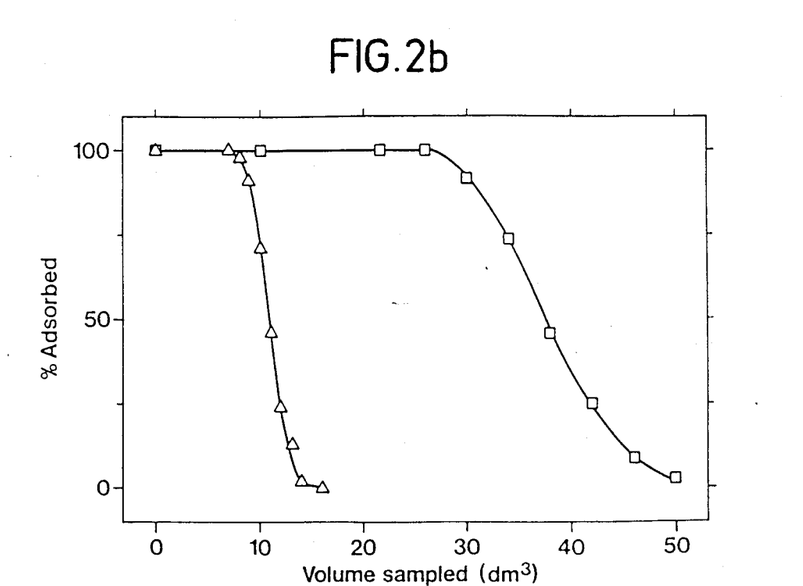
Figure 2C:
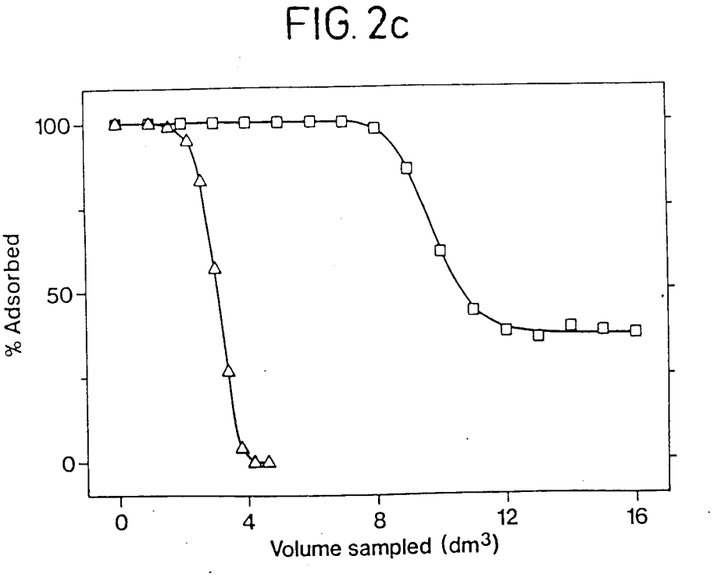

The tests were carried out at the following temperatures and relative humidities:

FIG. 2(a) Temperature: 20° C.; relative humidity: 10, 30 and 50% RH, respectively, from left to right.

FIG. 2(b) Temperature: +4° C.; relative humidity: 10% RH (Δ) and 50% RH (□).

FIG. 2(c) Temperature: 38° C.; relative humidity: 10% RH (Δ) and 50% RH (□).

IV. Storage test:

As the invention with the adsorbent is stabilization of the sampled sulfur dioxide it is essential that the storage capacity after sampling is investigated. As the samples as a rule are analyzed within a week after their arrival in the laboratory a storage test for two weeks is sufficient. Moreover, the stability was investigated at storage at room temperature and in refrigerator temperature which are the most common storage methods. As mentioned above the humidity of air is essential in sampling. Therefore the stability at different humidity degrees was also investigated. The prepared adsorbent well satisfied the above demands. After storage for a week there were still more than 95% left of the sulfur dioxide in the sample.

V. Importance of desorption time

A number of different desorption times were tested for determination of the shortest possible time of quantitative desorption and as a control of the fact that the stabilization also functioned during this step. Moreover, the influence on the desorption by treatment of the desorption solution containing the adsorbent was investigated by means of ultrasonics. In all cases 200 mg of adsorbnt were desorbed in 5 ml through Millipore deionized water. A compilation of the results of these experiments is found in table 1.

TABLE 1

Shows the yield in % of applied $SO_2$ (g) as a function of the desorption time. During the desorption those tubes, which were not ultrasonically treated, were turned twice. The tubes had been stored for 24 hours between application and desorption

| Desorption time | Desorbed $SO_2$ in % of generated |
|---|---|
| 5 min | 82 |
| 15 min | 97 |
| 1 h | 100 |
| 4 h | 100 |
| 5 min (ultrasonically treated) | 91 |

The desorption is apparently complete after one hour. The reason for such a long time being necessary is probably that the diffusion in the solid phase is relatively low. After four hours the yield is still on the same high level, which must be considered quite sufficient.

VI. Final determination

Two different methods are especially suitable for the final determination. Except for the pararosaniline method which is the best suited one for routine analyses, ion chromatography can also be used. The latter method (which is disclosed in Hamish Small, Timothy S. Stevens and William C. Bauman; "Novel Ion Exchange Chromatographic Method Using Conductometric Detection", Anal. Chem., 47 (1975) 1801–09, and the content of which is hereby included by reference) has its strong point in the fact that in addition to sulfur dioxide in the sample, it is also possible to get an idea about other inorganic ions adhered to the absorbent. If test atmosphere containing merely sulfur dioxide in air is tested one can see from the sulfate signal if oxidation of sulfur dioxide has taken place. Measurement carried out by means of this method indicate that oxidation only takes place to a very limited extent. Thus, it should also be possible to detect sulfur trioxide and mist of sulfuric acid in air. However, one disadvantage of this method is that the equipment is so expensive that so far it is only found in a few number of laboratories.

In the work cited above (the content of which is hereby included by reference) Dasgupta et al, has shown that it is possible to determine sulfur dioxide sampled as an adduct with formaldehyde by means of basic hydrolysis of this before it is added to the acid pararosaniline reagent. At acidification the adduct will not be regenerated as the kinetics of this reaction is reduced as a consequence of the low pH of the final solution. This method has been modified so that it can be used for the final determination in the method according to the invention. Certain parameters were then also controlled e.g. pH and time dependence of the basic hydrolysis, as is described below.

(1) Influence of the hydrolysis time

After the adsorbent has been desorbed the adduct must be hydrolyzed basically in order that the sulfite ions might be released from the aldehyde, as the adduct is too stable to be able to react directly with the color reagent. The time of this hydrolysis appeared to be critical for the yield in the final determination.

Figure 1:
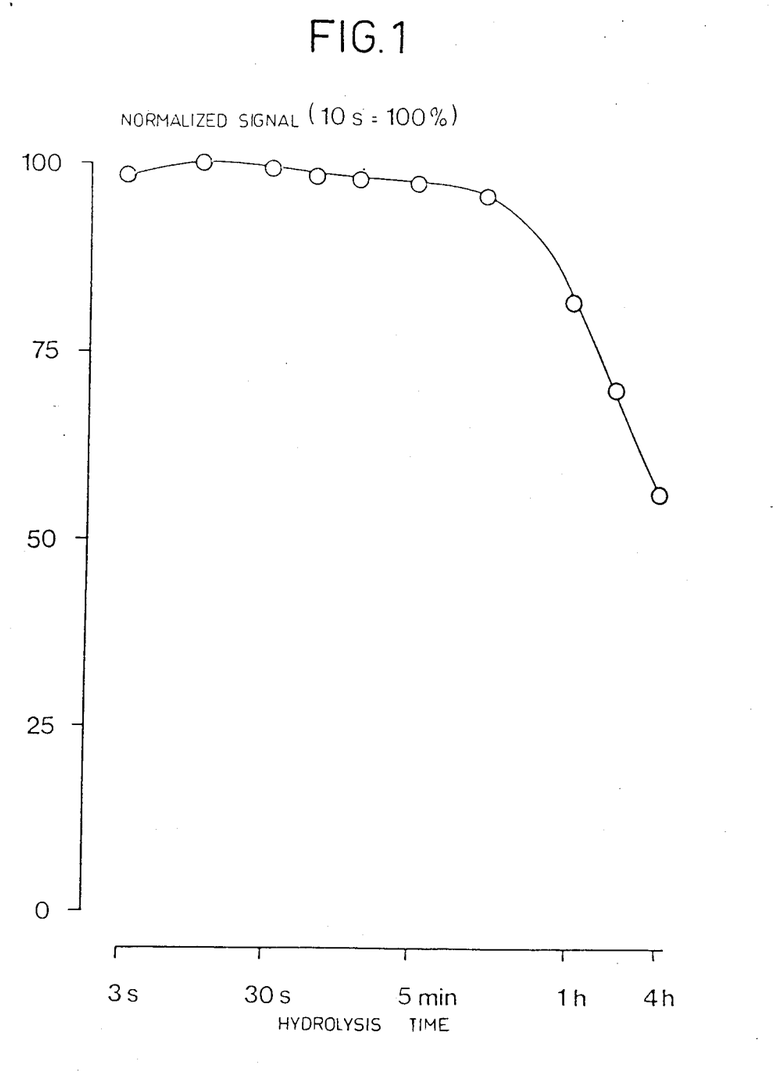
FIG. 1 shows the influence of the hydrolysis time on the amount determined in the final step.

The test was carried out in such a way that the compound was desorbed in 5 ml water as above. 2 ml of the solution were mixed with 1 ml of a solution of 0.5M NaOH and 0.02M HCHO in water. After the end of the hydrolysis time this mixture was added with a strong jet from an air displacement pipette to 1 ml of 250 ppm of pararosaniline in 1-M HCl. It is important that this order of addition is followed and the pararosaniline reagent is not added to the hydrolysate as it is desired to reduce pH therein as fast as possible. The reaction is quick and only after 10 seconds a complete hydrolysis has been obtained at determination of a typical sample having a content corresponding to the hygienic limit value (5 mg $m^{-3}$) by sampling at 200 ml/min for 15 min. If the hydrolysis is allowed to go on for a longer time the signal is reduced probably due to the fact that the sulfite ions are oxidized. The reason for this is that the stabilizer does not function at the high pH-value used in the hydrolysis step. After 15 min. a reduction corresponding to 5% of the signal has occurred. In FIG. 1 the resulting signal is shown as a function of the time, the time axis being logarithmic.

(2) Influence of the formaldehyde concentration

Formaldehyde is included as one of the necessary reagents in the Schiff-base reaction which gives the colored complex used for quantification of sulfur dioxide in the pararosaniline method. This method is disclosed in Scaringelli, F. P.; Saltzman, B. E.; Frey, S. A. Anal. Chem. 1967, 39, 1709-19, the content of which is hereby included by reference. It is not quite made clear how the reaction proceeds and it has been thought for a long time that an intermediary step in the color reaction is the formation of hydroxymethyl sulfonic acid. However, it has been found that if sulfur dioxide is added in the form of this compound to acidic pararosaniline no color is formed. Furthermore, if too much formaldehyde is added a similar color reaction is obtained although sulfur dioxide is not present and the blank value increases resulting in an inferior detection limit.

Figure 4:
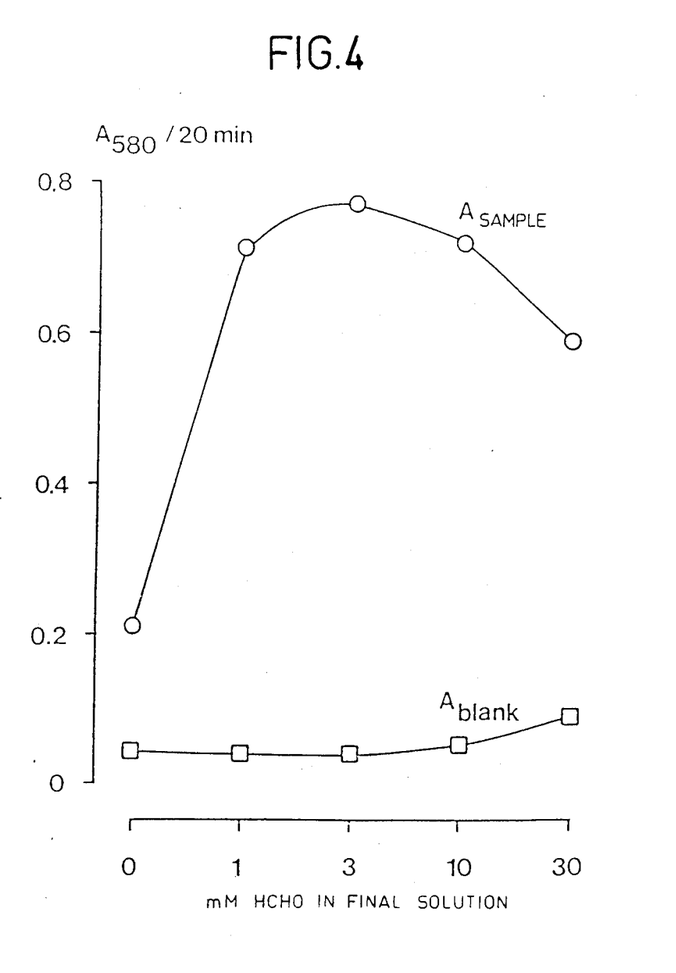
FIG. 4 shows the influence of added amount of HCHO on the amount determined in the final step.

Consequently there is an optimal formaldehyde concentration where the ratio of signal to background is as most favorable. For determinatin of this a test was carried out where the formaldehyde concentration in the final solution was varied between 1 and 30 mM. In the tests a solution was used as sample consisting of 50-μM glyoxal-bisulfite and 100-mM glyoxal in water. 0.5 ml of 0.5-M NaOH containing the necessary amount of formaldehyde was added to 1 ml of this solution. After 5 min. this solution was rapidly added to 0.5 ml of 250 ppm pararosaniline.HCl in 1-M HCl and $A_{580}$ was read after 15 min. By determining size and distribution of both signal and background the optimal content of formaldehyde could be decided. This was found to lie at 5 mM in the current conditions. In FIG. 4 the resulting absorbancy values are shown as plotted against the concentration of HCHO.

(3) Influence of glyoxal on the color reaction:

Since glyoxal does not function as aldehyde in the same way as formaldehyde in the color reaction, it was checked that it does not inhibit the color reaction to any large extent. With the glyoxal contents, i.e. about 50 mM, arising in the test solution, in this case no inhibition of the color reaction appeared.

(4) Dependence of pH in the final solution:

Both the reaction kinetics of the color formation and the background color arising from pararosaniline at pH-increase are factors strongly influenced by pH in the final solution where the color intensity is measured. Measurements were carried out to determine the optimal pH-value with respect to net signal and distribution when 50 mM glyoxal is included in the solution. Both signal and distribution influence the detection limit and the precision in the final determination. It was found that optimum lies at about pH=1.0 also when glyoxal is present.

(5) Kinetics of the color reaction

Figure 3:
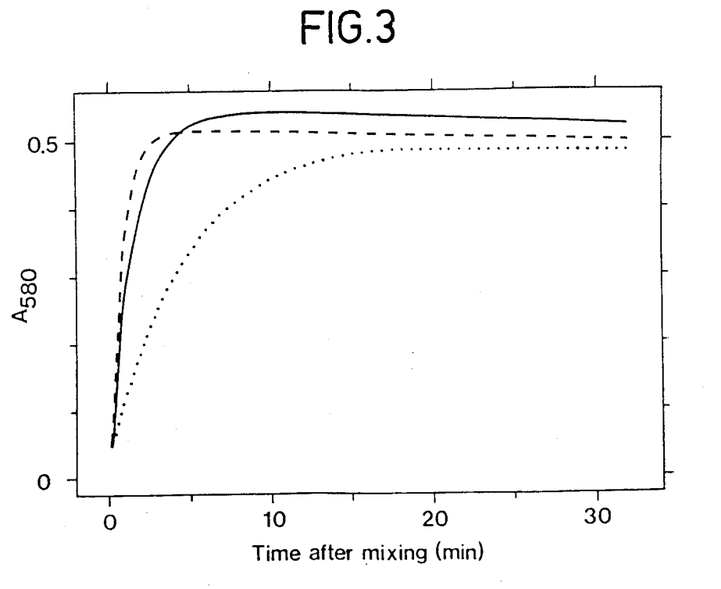
FIG. 3 shows the influence of the time between addition of reagent and measurement on the amount determined in the final step.

The course of the color development was studied in order to establich within which time limits addition of reagent and measurement must be accomplished. In FIG. 3 it is shown how $A_{580}$ is changed as a function of the time at about 24° C. and at different formaldehyde concentrations in the mixed base. In FIG. 3 the dotted line denotes 5 mM, the solid line 20 mM and the dashed line 50 mM formaldehyde. The variation in temperature is due to the fact that the mixing reaction is exothermic, as part of the hydrochloric acid in the pararosaniline reagent is neutralized by the sodium hydroxide in the hydrolysis mixture. However, such a variation can be allowed as the absorbancy curve shows a rather big plateau at absorbancy maximum. However, at manual measurements the time between mixture and measurement should lie within 10-15 min if reproducible results are to be obtained.

(6) Possibility of automatization of the final determination

The nature of the final determination method makes it very well suited to be transferred to an automatic analysis system. As the pararosaniline used in the color reaction is carcenogenic this means a safer handling as the solution is in a closed system during the whole reaction course. Such a method can be based on so-called "Flow Injections Analysis".

(7) Standardization:

The sodium bisulfite which is bought contains varying and occasionally rather great amounts of sulfate. The ideal is if standards of the same material as the sample, thus in this case of glyoxal-bisulfite, can be used. Problems will arise if, after synthesis of this standards, one does not know with certainty if there is a ratio of 1:1 between glyoxal and bisulfite. The sulfur dioxide carbonyl adducts are also very hygroscopic so that it is not possible to know with certainty whether one has succeeded in drying a salt sufficiently.

According to the invention a safe standard was obtained in the following way: 10 mM of glyoxal-bisulfite were prepared by leading 10.0 mmol of $SO_2(g)$ into a solution of 25 mmol formic acid, 20 mmol of NaOH and 10 mmol of glyoxal diluted to about 200 ml in water. After addition of gas the solution was diluted to 1000 ml with water. The added sulfur dioxide will reduce pH in the solution. However, the system with formic acid and formate will buffer so that pH in the stock standard will be about 4.0, i.e. close to the stability maximum of glyoxal-bisulfite. The purity of the gas is 99.97% and in this way it is possible to make a gravimetric standard with a known content of glyoxal-bisulfite. This standard was controlled by means of ion chromatography and was found to contain less than 0.5% of total sulfur amount as sulfate. In use no significant decrease of sulfite content could be observed after two months as determined by means of the pararosaniline method.

EXAMPLE 1

The tubes described here are only intended for use at sampling with equipment carried by a person for short time periods when a maximum value for exposure for a period of e.g. 15 min is to be measured. The pumps used at this type of sampling are substantially of membrane type. In these there is a counting unit counting the number of strokes made by the pump and as the pump is calibrated in cm³ per stroke one can then calculate the sampled volume. The flow rate through the tube in sampling should be 200 ml/min.

In sampling a sampling tube containing the adsorbent prepared in section 1 is opened by breaking the molten glass end of the tube, after which the tube is mounted in a container for this purpose on the clothes of the person carrying out the sampling near his respiratory zone with the white PTFE-wool in the tube turned away from the pump. The pump is started and a suitable volume of air is sampled with a flow that must not exceed 250 ml/min. The total volume of sampled air must not be greater than 3 dm³. After finished sampling the tube is again sealed with accompanying plastic caps and is sent to a laboratory for analysis.

At the analysis the stabilized sulfur dioxide is first released with 6 ml of water. This is allowed to proceed for at least one hour and meanwhile the tubes are turned a couple of times. 1 ml of a solution of 0.5-M of sodium hydroxide and 0.02-M of formaldehyde in water are added to 2 ml of this test solution. The reaction is allowed to proceed between 30 seconds and 2 min after which 2 ml of the hydrolysate are added by means of a bulb pipette to 1 ml of 250 ppm pararosanilinehydrochloride in 1-M HCl. The order of addition is imporant. One must not add the color reagent to the hydrolysate.

After additional 10 min the intensity of the formed color complex is measured in a spectrophotometer by means of a 1-cm cuvette at the wavelength 580 nm against a blank that has undergone the same hydrolysis procedure as the sample. A content corresponding to the hygienic limit value gives a signal of about 1 AU under these conditions.

Should the signal be considerably greater than this the remaining 3 ml of the test solution can be diluted to a suitable content. Otherwise it is used as a double test. Evaluation of the content of sulfur dioxide in the leach water is made against standards prepared either by dissolving commercially available dried glyoxal-bisulfite disodium salt dihydrate in 50 mM glyoxal or preferably by preparing a standard in glyoxal from sulfur dioxide gas of 99.97%, which can be bought in an aerosol can at a low cost. The standard solution must also go through the same hydrolysis procedure. The content of sulfur dioxide of the sampled air is then calculated as based on the content of sulfur dioxide in the test solution.

EXAMPLE 2

The tubes were field tested and compared to the method of Dasgupta et al (loc. cit.) in a sulfite paper pulping plant at sulfur dioxide concentrations from 12 to 160 mg/m³. Temperature and relative humidity at the sampling site was approximately 25° C. and 20% RH, respectively. Four samples were taken simultaneously for 15 minutes from a common sampling port with two sorbent tubes containing 200±10 mg sorbent and two midget spill-proof fritted glass impinger flasks containing 10 ml buffered formaldehyde absorber (Dasgupta et al, loc. cit), using an SKC HFS 113 sampling pump with four 200 ml/min (nominally) flow restrictors. Flow rates were checked several times before, during and after the sampling session. Sampling sites were chosen so as to maximize the variation in $SO_2(g)$ concentration. Some tubes were desorbed directly and stored in a refrigerator for 7 days, while the remaining tubes were divided and stored for the same amount of time, half of them in a refrigerator and the rest at room temperature under fluorescent light. Desorption and analysis of S(IV) was done according to the above description while the buffered formaldehyde absorber solutions were determined according to the procedure recommended by Dasgupta et al (loc. cit.).

Figure 5:
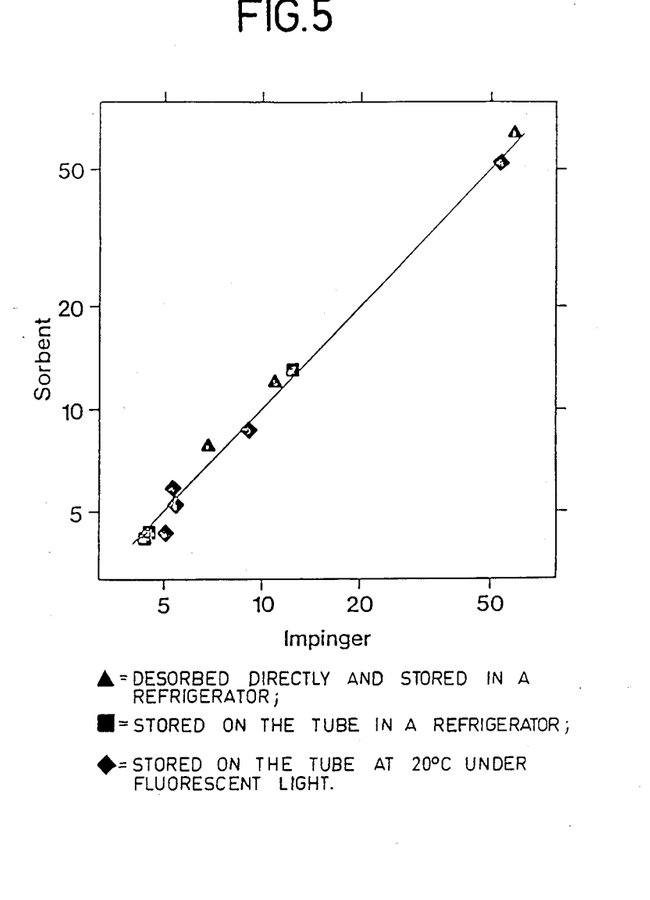
FIG. 5 shows a plot of concentrations found with solid adsorbent and buffered formaldehyde impinger method.

The numerical results from these tests are compiled in Table 2 and visualized as a plot of the results obtained with the sorbent tubes vs. those obtained with the buffered formaldehyde impinger method in FIG. 5. The concentrations are given in mg $SO_2(g)/m^3$ and a logarithmic scaling of the axes is used. Standard deviations for the differences between duplicate runs within each sampling method were calculated and tested for difference by F-test. The test gave a F-value of 49.5, which makes the precision difference sigificant ($F_{10,10}=2.98$ at 95% confidence level), i.e. the impinger method has a precision inferior to the adsorbent tubes with the equipment used. Most of the uncertainty in the results are due to problems in maintaining a constant flow with the state of the art sampling pumps. This was especially noticeable with the impingers, where the flow resistance was considerably higher than with the tubes and varied somewhat during the run. The adsorbent tubes were easier to use in this aspect, and pump flow calibrations could be made less frequent than with the impingers.

Figure 6:
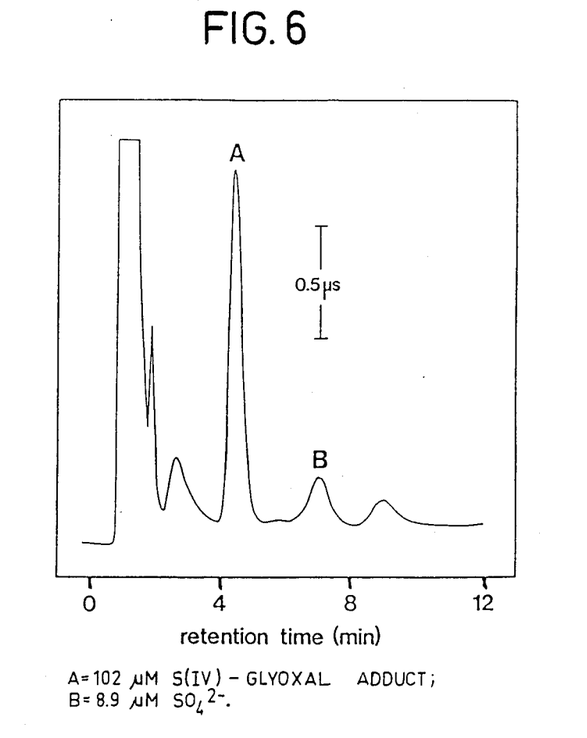
FIG. 6 shows a ion chromatogram of a desorbed adsorbent solution.

An ion chromatogram of one of the adsorbent tube samples from the field test can be seen in FIG. 6. A random sample from the field test stored on the adsorbent 1 week at 20° C. before desorption and 2 weeks in the desorption solution has been used.

TABLE 2

| | | Results from the field test | | | | | |
| | | concentrations found (mg $SO_2(g)/m^3$) by | | | | difference[b] | |
| sample # | storage[a] | impinger 1 | impinger 2 | sorbent 1 | sorbent 2 | impinger | sorbent |
|---|---|---|---|---|---|---|---|
| 1 | DD | 6.7 | 7.0 | 7.7 | 7.8 | −0.3 | −0.1 |
| 2 | DD | 11.1 | 10.9 | 12.0 | 11.9 | 0.2 | 0.1 |
| 3 | DD | 62.1 | 55.9 | 64.4 | 63.6 | 6.2 | 0.8 |
| 4 | RE | 4.4 | 4.6 | 4.3 | 4.3 | −0.2 | ±0 |
| 5 | RE | 4.7 | 4.1 | 4.2 | 4.1 | 0.6 | 0.1 |
| 6 | RE | 12.9 | 11.9 | 12.9 | 13.0 | 1.0 | −0.1 |
| 7 | RT | 5.0 | 5.2 | 4.3 | 4.4 | −0.2 | −0.1 |
| 8 | RT | 5.5 | 5.4 | 5.4 | 5.1 | 0.1 | 0.3 |
| 9 | RT | 5.3 | 5.4 | 6.3 | 5.4 | −0.1 | 0.9 |
| 10 | RT | 9.2 | 9.0 | 8.9 | 8.3 | 0.2 | 0.6 |
| 11 | RT | 57.6 | 50.2 | 52.8 | 52.1 | 7.4 | 0.7 |

Statistics for the differences:

TABLE 2-continued

| | | Results from the field test | | | | | |
| | | concentrations found (mg $SO_2(g)/m^3$) by | | | | difference[b] | |
| sample # | storage[a] | impinger 1 | impinger 2 | sorbent 1 | sorbent 2 | impinger | sorbent |
| | Impinger: | 1.35 ± 2.73 | | | | | |
| | Sorbent: | 0.29 ± 0.39 | | $F = \left(\frac{2.73}{0.39}\right)^2 = 49.5$ | | | |

Samples were stored 7 days between sampling and determination.
[a]DD = desorbed directly after sampling and stored in a refrigerator;
RE = tube stored in a refrigerator;
RT = tube stored at room temperature under fluorescent light.
[b]Difference between channel 1 and 2 for each method

What is claimed is:

1. A method of measuring the content of a compound in air comprising the steps of:
   (a) adsorbing the compound from air on a solid adsorbent, said solid adsorbent including a carrier consisting of an ion exchange material and a stabilizer; wherein
      (i) said exchange material is partially regenerated so as to provide a buffering action towards acidic and basic compounds in order to maintain pH on said solid adsorbent within a preselected range of optimum stability for said compound which is sampled; and
      (ii) said stabilizer being selected from the group consisting of a stabilizer for the compound to be adsorbed and a stabilizer for a reaction product of said compound, which reaction product is formed in the adsorption;
   (b) measuring the amount of the compound in a form in which it is adsorbed.

2. The method of claim 1 wherein said ion exchange material forming the carrier gives a pH-value of lower than 8.

3. The method of claim 2, wherein said ion exchange material gives a pH-value of 4–5.

4. The method of claim 1, wherein the carrier consists of a weak ion exchange material.

5. The method of claim 4, wherein the ion exchange material is a weak cation exchange material containing polyacrylic acid.

6. The method of claim 1, wherein the carrier has a pka-value of about 5 and is regenerated so as to have 50% of its active groups in $H^+$-form and 50% in $Na^+$-form.

7. A method for measuring the content of a compound in air comprising the steps of:
   (a) adsorbing the compound from air on a solid adsorbent, said solid adsorbent including a carrier consisting of an ion exchange material, wherein the carrier has a pka value of about 5 and is regenerated so as to have 50% of its active groups in $H^+$-form and 50% in $Na^+$-form; and
   (b) measuring the amount of the compound in a form in which it is adsorbed.

8. The method of claim 7, wherein said compound to be measured is sulfur dioxide and wherein the adsorbent comprises an aldehyde as a stabilizer for hydrogen sulfite which is formed from sulfur dioxide in the adsorption.

9. The method of claim 7, wherein the aldehyde is selected from the group consisting of formaldehyde, acetaldehyde, chloral and glyoxal.

10. The method of claim 9, wherein the aldehyde is glyoxal.

11. A solid adsorbent for measurement of the content of sulfur dioxide, hydrogen sulfite being formed, comprising:
    (a) a carrier consisting of an ion exchange material, said exchange material having a pka value of about 5 and having been regenerated so as to have 50% of its active group in $H^+$-form and 50% in $Na^+$-form; and
    (b) a stabilizer for adsorbed hydrosulfite consisting of an aldehyde.

12. The adsorbent as claimed in claim 11, wherein the aldehyde is formaldehyde.

13. The adsorbent as claimed in claim 11, wherein the ion exchange material forming the carrier is formed from a material which yields a pH-value lower than 8.

14. The adsorbent as claimed in claim 13, wherein the solid buffer is formed from a material which yields a pH-value of 4–5.

15. The adsorbent as claimed in claim 11, wherein the carrier is a weak ion exchange material.

16. The adsorbent as claim in claim 15, wherein the ion exchange material is a weak cation exchange material containing polyacrylic acid.

17. A solid adsorbent for measurement of the content of sulfur dioxide, hydrogen sulfite being formed, comprising:
    (a) a carrier consisting of an ion exchange material, said exchange material having a pka value of about 5 and having been regenerated so as to have 50% of its active groups in $H^+$-form and 50% in $Na^+$-form; and
    (b) a stabilizer for adsorbed hydrosulfite consisting of glyoxal.

* * * * *